United States Patent [19]

Zuech

[11] 4,010,217
[45] Mar. 1, 1977

[54] OLEFIN CONVERSION

[75] Inventor: Ernest A. Zuech, Bartlesville, Okla.

[73] Assignee: Phillips Petroleum Company, Bartlesville, Okla.

[22] Filed: Feb. 10, 1975

[21] Appl. No.: 548,582

Related U.S. Application Data

[60] Continuation of Ser. No. 267,998, June 30, 1972, abandoned, which is a division of Ser. No. 73,231, Sept. 17, 1970, Pat. No. 3,691,144, which is a division of Ser. No. 717,023, March 28, 1968, Pat. No. 3,558,518, which is a continuation-in-part of Ser. No. 694,873, Jan. 2, 1968, abandoned, and Ser. No. 635,700, May 3, 1967, abandoned.

[52] U.S. Cl. .................. 260/683 D; 260/648 R; 260/649 R; 260/658 R; 260/666 A; 260/677 R; 260/680 R
[51] Int. Cl.² .................................... C07C 3/62
[58] Field of Search ....... 260/666 A, 683 D, 680 R, 260/677 R, 658 R, 648 R, 649 R

[56] References Cited

UNITED STATES PATENTS

| | | | |
|---|---|---|---|
| 3,558,518 | 1/1971 | Zuech | 260/683 |
| 3,691,144 | 9/1972 | Zuech | 260/683 |
| 3,703,561 | 11/1972 | Kubicek et al. | 260/683 |
| 3,708,551 | 1/1973 | Kittleman et al. | 260/683 |

*Primary Examiner*—D. Horwitz
*Assistant Examiner*—C. E. Spresser

[57] ABSTRACT

A process for the conversion of olefinic hydrocarbons according to the olefin reaction (e.g., the olefin disproportionation reaction) by contacting the olefinic hydrocarbon with a catalyst comprising a coordination compound of molybdenum or tungsten complexed with NO, together with an organoaluminum adjuvant.

13 Claims, No Drawings

OLEFIN CONVERSION

This application is a continuation of copending application Ser. No. 267,998, filed June 30, 1972, now abandoned, which is a divisional of application Ser. No. 73,231, filed Sept. 17, 1970, now U.S. Pat. No. 3,691,144, which is a divisional of application Ser. No. 717,023, filed Mar. 28, 1968, now U.S. Pat. No. 3,558,518, which is a continuation-in-part of application Ser. No. 694,873, filed Jan. 2, 1968, now abandoned, and application Ser. No. 635,700, filed May 3, 1967, now abandoned.

This invention relates to the conversion of olefin hydrocarbons and to a homogeneous catalyst system for such conversion. In one aspect this invention relates to the olefin reaction. In another aspect it relates to the conversion of olefins to other olefins having different molecular weights. In still another aspect it relates to a novel homogeneous catalyst system.

The term olefin reaction, as used herein, is defined as a process for the catalytic conversion over a catalyst of a feed comprising one or more ethylenically unsaturated compounds to produce a resulting product which contains at least ten percent by weight of product compounds, which product compounds can be visualized as resulting from at least one primary reaction, as defined below, or the combination of at least one primary reaction and at least one unsaturated bond isomerization reaction, and wherein the sum of the compounds contained in said resulting product consisting of hydrogen saturated hydrocarbons, and compounds which can be visualized as formed by skeletal isomerization but which cannot be visualized as formed by one or more of the above-noted reactions, comprises less than twenty-five percent by weight of the total of said resulting product. Feed components and unsaturated bond isomers thereof are not included in the resulting product for the purpose of determining the abovenoted percentages.

In the olefin reaction as defined above, the primary reaction is a reaction which can be visualized as comprising the breaking of two existing unsaturated bonds between first and second carbon atoms and between third and fourth carbon atoms, respectively, and the formation of two new unsaturated bonds. Said first and second carbon atoms and said third and fourth carbon atoms can be in the same or different molecules. The olefin reaction according to this invention is illustrated by the following reactions.

1. The disporportionation of an acyclic mono- or polyene having at least three carbon atoms into other acyclic mono- or polyenes of both higher and lower number of carbon atoms; for example, the disproportionation of propylene yields ethylene and butenes; the disproportionation of 1,5-hexadiene yields ethylene and 1,5,9-decatriene;

2. The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene;

3. The conversion of ethylene and an internal acyclic mono- or polyene having four or more carbon atoms to produce other olefins having a lower number of carbon atoms than that of the acyclic mono- or polyene; for example, the conversion of ethylene and 4-methylpentene-2 yields 3-methylbutene-1 and propylene;

4. The conversion of ethylene or an acyclic mono- or polyene having three or more carbon atoms and a cyclic mono- or cyclic polyene to produce an acyclic polyene having a higher number of carbon atoms than that of any of the starting materials; for example, the conversion of cyclooctene and 2-pentene yields 2,10-tridecadiene; the conversion of 1,5-cyclooctadiene and ethylene yields 1,5,9-decatriene;

5. The conversion of one or more cyclic mono-or cyclic polyenes to produce a cyclic polyene having a higher number of carbon atoms than any of the starting materials; for example, the conversion of cyclopentene yields 1,6-cyclodecadiene, and continued reaction can produce still higher molecular weight materials;

6. The conversion of an acyclic polyene having at least seven carbon atoms and having at least five carbon atoms between any two double bonds to produce acyclic and cyclic mono- and polyenes having a lower number of carbon atoms than that of the feed; for example, the conversion of 1,7-octadiene yields cyclohexene and ethylene; or 7. The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

New catalytic processes have been discovered, in recent years, for the conversion of olefins to other olefinic products including products of both higher and lower molecular weight whereby olefins of relatively low value are converted into olefins of higher value. Such conversions have been carried out with heterogeneous catalysts such as those comprising compounds of molybdenum or tungsten which are usually associated with support materials such as alumina or silica. It has not been found that these olefin conversions can be carried out in a substantially homogeneous state using, as catalysts, selected coordination compounds of molybdenum or tungsten in combination with suitable catalytic adjuvants to produce olefins products of increased value including solid products, for example, rubber suitable for the manufacture of tires, wire coating, footwear and other industrial products.

It is object of this invention to provide a method and a catalyst system for the conversion of olefin hydrocarbons. It is also an object of this invention to provide a homogeneous catalyst comprising coordination compounds of molybdenum or tungsten together with a catalytic adjuvant for the olefin reaction. Still another object is to provide a method for converting olefins to other olefins of higher and lower number of carbon atoms. The provision of a homogeneous coordination catalyst of molybdenum or tungsten together with a catalytic adjuvant for converting olefins to other olefins according to the olefin reaction is yet another object of this invention. Other aspects, objects and advantages of the invention will be apparent to one skilled in the art upon study of the disclosure including the detailed description of the invention.

According to the process of this invention, olefinic compounds are converted to other olefinic materials by contact with a catalyst which forms, under catalyst forming conditions, by the admixture of a. a coordination compound having the formula $[(L)_a M_b(NO)_c Z_d]_x$ wherein M is molybdenum or tungsten; (L) is an organic or inorganic ligand as hereinafter described; Z is a halogen, CN, SCN, OCN, SnCl$_3$, or a carboxylic acid radical; $a$ is 0–3; $b$ is generally 1–2, $c$ is 1–2, $d$ is 0–5, and the number of (L), NO, and Z groups present in the complex is not greater than the number required for the metal to achieve the closed shell electronic configuration of the next higher atomic number inert gas; $x$ is a number indicating the polymeric state of the compound and is generally 1 or 2; with b. an aluminum-containing catalytic adjuvant selected from
 1. R$_e$AlX$_f$,
 2. a mixture of compounds of (1),
 3. a mixture of one or more of AlX$_3$ or R$_e$AlX$_f$ compounds with one or more compounds having the formula R$_g^1$M$^1$X$_h$, or
 4. an AlX$_3$ compound, wherein each R is an aormatic or saturated aliphatic hydrocarbon radical having up to 20 carbon atoms including alkoxy and halo derivatives thereof, preferably an alkyl radical having up to 10 carbon atoms; each R$^1$ is hydrogen or R; each X is a halogen; each M$^1$ is a metal of Group IA, IIA, IIB or IIIA; $e$ is 1, 2 or 3, $f$ is 0, 1 or 2, the sum of $e$ and $f$ being 3; $g$ is 1, 2 or 3, $h$ is 0, 1 or 2, the sum of $g$ and $h$ being equal to the valence of M$^1$; when the adjuvant is (1) and acyclic olefins are converted, $f$ is preferably 1 or 2.

The elements referred to herein are in accordance with the Periodic Table of Elements appearing in Handbook of Chemistry and Physics, Chemical Rubber Company, 45th edition (1964).

Some specific examples of R$_e$AlX$_f$ and AlX$_3$ compounds are: methylaluminum sesquichloride, methylaluminum dichloride, dimethylaluminum fluoride, ethylaluminum dichloride, aluminum trichloride, ethylaluminum sesquichloride, diethylaluminum chloride, di(3-ethoxypropyl)aluminum bromide, di(methoxymethyl)aluminum bromide, n-pentylaluminum dichloride, aluminum tribromide, di(2-ethylhexyl)aluminum bromide, phenylaluminum dichloride, benzylaluminum diiodide, di(4,4,4-trifluorobutyl)aluminum chloride, dieicosylaluminum bromide, and the like, and mixtures thereof.

Some specific examples of the R$_g^1$M$^1$X$_h$ compounds are: phenyllithium, benzylrubidium, methylsodium, t-butylpotassium, lithium hydride, anthrylcesium, ethylberyllium hydride, lithium aluminum hydride, lithium borohydride, methylcadmium chloride, diethylzinc, dicyclohexylmercury, methylgallium dibromide, triethylaluminum, di(12-chlorododecyl)aluminum chloride, dimethylbarium, boron trifluoride, triethylindium, triisopropylthallium, dimethylcalcium, dimethylstrontium, hexylzinc iodide, and the like and mixtures thereof.

Presently preferred (b) adjuvant components of the catalytic system are those shown in (1) and (2), particularly adjuvants such as those represented by R$_3$Al$_2$X$_3$, and RAlX$_2$. Adjuvants such as methylaluminum sesquichloride and ethylaluminum dichloride are frequently favored because they generally provide increased catalytic activity. Methylaluminum sesquichloride is most preferred when greater selectivity to desired products is required.

Some ligands (L) which can be present in the VIB complex component (a) of the present invention include those represented by the formulas:

R$_3$Q; R$_3$QO; R$_2$Q—QR$_2$; CO; NO; O; S;

R$_3$N; R$_2$N-R$^2$-NR$_2$;

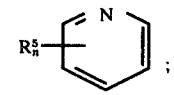

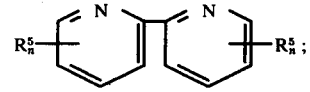

R—S—R; R$^3$S; (CHR$^4$—CR$^4$—CH$_2$)$_r$; R(CN)$_b$;

(R$_2$NCSS)$_r$; [(RCO)$_2$CH]$_r$; or R(COO)$_b$;

wherein each R is an aromatic or saturated aliphatic hydrocarbon radical, including alkoxy and halo derivatives thereof, having up to 20 carbon atoms; Q is one of phosphorus, antimony, or arsenic; R$^2$ is a divalent aromatic or saturated aliphatic hydrocarbon radical having up to 20 carbon atoms R$^3$ is a saturated or ethylenically unsaturated divalent hydrocarbon radical having 3 to 10 carbon atoms; each R$^4$ is hydrogen or a methyl radical; each R$^5$ is an aromatic, saturated aliphatic, or ethylenically unsaturated aliphatic hydrocarbon radical, having up to 20 carbon atoms; $n$ is 0, 1, 2 or 3; and $m$ is 0, 1, 2, 3, 4 or 5.

The (a) component of the catalyst is formed by treating a tungsten or molybdenum halide or a salt of an organic acid having 1 to about 30 carbon atoms per molecule with NO or nitrosyl halide alone or in the presence of one or more ligand-forming compounds comprising organic phospines, organic arsines, organic stibines, organic diphosphines, carbon monoxide, organic sulfides, substituted and unsubstituted cylclopentadienyl compounds, allyl compounds, crotyl compounds, methallyl compounds beta-diketones, or hydrocarbyl substituted dithiocarbamates, where sufficient ligand-forming groups are added to satisfy the electronic requirements of the coordinate complex.

The (a) component of the catalyst system of the present invention can be the reaction product, under catalyst-forming condition, of a molybdenum or tungsten compound, such as a hexacarbonyl, oxide, sulfide, halide, oxyhalide, or a salt of an organic or inorganic acid, preferably a halide, with NO or a nitrosyl halide, or a combination of NO and a nitrosyl halide and one or more coordinating materials selected from

R$_3$Q; R$_3$QO; R$_2$Q—QR$_2$; CO;

radical-containing compounds; R$_3$N; R$_2$N-R$^2$—NR$_2$;

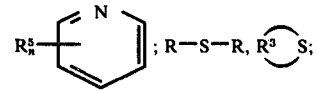

; R—S—R, R$^3$S;

(CHR$^4$=CR$^4$—CH$_2$)- radical-containing compounds; R(CN)$_b$;

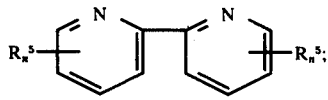

($R_2NCSS$)- radical-containing compounds;
$RCOCH_2COR$; or $R(COO)_2$ radical-containing compounds;

wherein each R is a saturated aliphatic or aromatic hydrocarbon radical having up to 20 carbon atoms including alkoxy and halo derivatives thereof, each Q is phosphorus, arsenic, or antimony; $R^2$ is a divalent saturated aliphatic or aromatic hydrocarbon radical having up to 20 carbon atoms; $R^3$ is a saturated or ethylenically unsaturated divalent hydrocarbon radical having 3 to 10 carbon atoms; each $R^4$ is hydrogen or a methyl radical, each $R^5$ is an aromatic, saturated aliphatic, or ethylenically unsaturated hydrocarbon radical having up to 30 carbon atoms; $m$ is 0–5, $n$ is 0–3, and $b$ is 1 or 2.

Some examples of molybdenum or tungsten starting materials are: $MoCl_5$, $MoBr_5$, $MoBr_2$, $MoBr_3$, $MoBr_4$, $MO(CO)_6$, $MoCl_2MoCl_3MoCl_4$, $MoF_6$, $MoI_2$, $MoO_2$, $MoS_2$, $MoO_2Br_2$, $MoOCl_4$, $MoO_2Cl_2$, $Mo_2O_3Cl_5$, $MoOF_4$, $WBr_2$, $WBr_5$, $WBr_6$, $WCl_2$, $WCl_4$, $WCl_5$, $WCl_6$, $WF_6$, $WI_2$, $WI_4$, $WOBr_4$, $WO_2Br_2$, $WOCl_4$, $WO_2Cl_2$ and $WOF_4$.

The preferred VIB complexes or component (a) of the present catalyst system are those which contain at least one halogen atom and, thus, it is generally preferred to use a nitrosyl halide in preference to NO when treating VIB starting compounds which do not already contain halogen. Nitrosyl halides, however, can also be used, if desired, to treat halogen-containing VIB starting compounds.

Some examples of specific coordinating materials for preparing the VIB metal complexes are: trimethylphosphine, triethylarsine, tri-t-butylstibine, tri-n-butylphosphine, triisopropylarsine, tri-n-nonylstibine, tri-n-decylphosphine, tri-n-pentadecylarsine, tri(6,8-di-n-butyldecyl)stibine, tri-n-eicosylphosphine, diethyl-n-tridecylarsine, tri(3,5-dimethylcyclohexyl)stibene, methyldi-n-octylphosphine, tricyclopentylarsine, methyldicylohexylstibine, tricyclohexylphosphine, tri(4-cyclohexylbutyl)arsine, tri(2,4,6-triethylphenyl)stibine, triphenylphosphine, diethylphenylarsine, methyldi(4-dodecylphenyl)stibine, tribenzylphosphine, tri(3,6-diphenyloctyl)arsine, triphenylphosphine oxide, tetramethyldiphosphine, tetrabenzyldistibine, tripentylarsine oxide, sodium cyclpentadienylide and lithium 2-methylcyclopentadienylide.

Amines such as: trimethylamine, tri-tert-butylamine, tri-n-decylamine, trieicosylamine, tricyclohexylamine, triphenylamine, tribenzylamine, ethyldi-n-tridecylamide, diisopropyl-4-tolylamine, tri(6-phenylhexyl)amine, tri(3,5-di-n-heptylcyclohexyl)amine, triphenylamine, N,N,N',N'-tetramethylethylenediamine, pyridine, 4-vinylpyridine, 4-(2-ethylhexyl)pyridine and 2,2'-bipyridyl.

Other materials include: butyl sulfide, phenyl sulfide, thiophene, 2.5-diethylthiophene, allyl bromide, methallyl chloride, crotyl iodine, tetrallyl tin, tetrakis(2-methyl-2-butenyl)tin, tetramethallyl tin, acetylacetone, 2,4-heptanedione, 2-methylpyridine, benzoic acid, stearic acid, lauric acid, butyronitrile, acetonitrile, sodium diethyldithiocarbamate, potassium dimethyldithiocarbamate and carbon monoxide.

Some examples of specific VIB complex (a) components are: (triphenylphosphine)$_2$Mo(NO)$_2$Cl$_2$, Mo(NO)$_2$Cl$_2$, (pyridine)$_2$Mo(NO)$_2$Cl$_2$, (stearate)$_2$Mo(NO)$_2$Cl$_2$, (benzoate)$_2$MO(NO)$_2$Cl$_2$, (triphenylphosphine)$_2$W(NO)$_2$Cl$_2$, NO-treated (butyronitrile)$_2$MoCl$_4$, NO-treated (cyclopentadienyl)MO(CO)$_3$I, NO-treated (stearate)$_2$MoCl$_2$, NO-treated pyridine-treated MoCl$_5$, NO-treated (benzoate)$_2$MoCl$_3$, No-treated (acetylacetonate)$_2$MoO$_2$, NO-treated MoOCl$_3$, NO-treated tetrallyltin-treated MoCl$_5$, NO-treated MoCl$_5$, NO-treated MoCl$_2$, NO-treated WCl$_6$, NO-treated tributylphosphine-treated MoCl$_5$, NO-treated benzoic acid-treated WCl$_6$, NOCl-treated MoO$_2$, NOCl-treated pyridine-treated MoO$_2$, NO-treated MoO$_2$, NOCl-treated (triphenylphosphine)$_2$W(CO)$_4$ and NO-treated MO(acetate)$_2$.

The formula $[(L)_aM_b(NO)_cZ_d]x$ is used herein to identify the product obtained by admixture, under catalyst forming conditions, of a molybdenum or tungsten compound such as a halide or salt of an organic acid having one to about 20 carbon atoms per molecule, with NO or nitrosyl halide or a combination of NO or NOCl and at least one complexing agent or ligand-forming compound, wherein sufficient (L), (NO) or Z groups are present to satisfy the electronic requirements of the coordination complex. In any event, it should be understood that the catalytic agent which has activity for the olefin reaction conversion is the product resulting from the admixture of the metal compound and NO, with or without a ligand-former; and then the admixture of the resulting product with the aluminum-containing adjuvant, all under catalyst forming conditions.

The (a) component of the catalyst is the reaction product obtained by combining the transition metal salt with NO in the presence of one or more coordinating materials. These reagents are simply combined under conditions of time and temperature which are sufficient to permit the complex to be formed. In such a preparation, the molar proportion of VIB metal compound to coordinating compound can be in the range of from about 10:1. The reaction product is obtained by combining these ingredients in the presence of excess nitric oxide at any convenient temperature; however, excessively high temperatures at which some of the components might tend to decompose and excessively low temperatures at which some of the components might tend to crystallize or otherwise tend to become unreactive should be avoided. It will usually be preferred to admix the ingredients at a temperature in the range of from about −25° to about 130° C., preferably 0° to about 60° C., for a time in the range of from a few seconds up to about 24 hours, preferably in the presence of a diluent in which the components of the reaction are at least partially soluble. Any convenient diluent such as methylene chloride, benzene, chlorobenzene, and the like, can be used for this purpose. Any order of addition can be used. Thus, for example, a VIB metal halide can be treated with NO, either in the presence or absence of a coordinating material.

In general, the (a) component of the catalyst system is fully prepared before contact is made with the (b) component or adjuvant. It is sometimes desirable to remove excess or unreacted NO or nitrosyl halides from the (a) component before contact is made with the (b) component. Such removal can be conveniently carried out by warming the complex under reduced pressure to evaporate the NO or nitrosyl halide. Such removal of this excess reagent is not a necessity but is frequently desirable, because the excess reagent appears to consume some of the (b) component which is added later. For this same reason, grossly excessive amounts of any of the complexing agents should be avoided.

The Group VIB complex or (a) component can be prepared either by contacting the VIB starting compound with the NO or nitrosyl halide followed by contact with the complexing agents, or, alternatively, by first contacting the VIB starting compound with the complexing agents and then with the NO or nitrosyl halide. Similarly, other combinations are possible such as treating the VIB compound with a complexing agent both before and after contact with the NO or nitrosyl halide.

The above-described (b) and (a) components of the catalyst system are generally combined, for use in this invention, the proportions in the range from about 0.1:1 to about 20:1, preferably from about 1:1 to 10:1, moles of the (b) component to moles of the (a) component. The catalyst is prepared simply by combining these catalyst components under conditions of time and temperature which permit the catalytically active catalyst to be formed. Excessively high temperatures and excessively low temperatures, as hereinbefore stated, should be avoided. This combination occurs very readily and, in general, the components can be mixed at any convenient temperature within the range of −80° to about 100° C., preferably 0°–60° C., for a few seconds or for periods up to several hours in the presence of a diluent in which both the components are at least partially soluble. Any convenient diluent such as benzene, xylene, toluene, cyclohexane, chlorobenzene, methylene chloride, ethylene chloride, and the like, can be used for this purpose. Halogenated diluents are generally preferred. The mixing of these two catalyst components is generally carried out in the substantial absence of air or moisture, generally in an inert atmosphere. After the catalytic mixture is formed, it need not be isolated but can be added directly to the reaction zone as a solution in its preparation solvent. If desired, the (a) and (b) catalyst components can be separately added, in any order, to the reaction zone either in the presence or absence of the feed olefin.

Olefins applicable for use in the process of the invention are non-tertiary, non-conjugated, acyclic mono- and polyenes having at least 3 carbon atoms per molecule including cycloalkyl, cycloalkenyl and aryl derivatives thereof; monocyclic mono- and polyenes and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3-30 carbon atoms per molecule and with such cyclic olefins having 4-30 carbon atoms per molecule. Non-tertiary olefins are those olefins wherein each carbon atom, which is attached to another carbon atom by means of a double bond, is also attached to at least one hydrogen atom.

Some specific examples of acyclic olefins suitable for reactions of this invention include propylene, 1-butene, 2-butene, 1-pentene, 2-pentene, 1-hexene, 1,4-hexadiene, 2-heptene, 4-methyl-2-octene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 4-methyl-4-octene, 4-vinylcyclohexene, 1,7-octadiene, 1,5-eicosadiene, 2-triacontene, 2,6-dodecadiene, 1,4,7,10,13-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 5,5,4,4-tetramethylcyclononene, 3,4,5,6,7-pentaethylcyclodecene, 1,5-cyclooctadiene, 1,5,9-cyclododecatriene, 1,4,7,10-cyclododecatetraene, 6-methyl-6-ethylcyclooctadiene-1,4, and the like, and mixtures thereof.

It will be understood by those skilled in the art that not all olefinic materials will be converted by the present invention with equal effectiveness. The reactions described in the present invention are equilibrium-limited reactions and, barring the selective removal of one or more products from the reaction zone, the extent of conversion will depend upon the thermodynamics of the specific system observed. Thus, conversion of olefinic materials to give specific products can be thermodynamically favored while the reverse reaction is very slow and ineffective. For example, 1,7-octadiene is converted to equilibrium-favored products such as cyclohexene and ethylene. The reverse reaction of ethylene and cyclohexene, correspondingly, goes very poorly. Other well-known factors, such as steric hindrance in bulky molecules, significantly and sometimes drastically affect the rates of reaction of some olefins such that extremely long reaction times are required.

The reaction of symmetrical monoolefins with themselves, to give different olefin products, will sometimes proceed very slowly, requiring some double bond migration to take place before the reaction will proceed at a significant rate. For the same reason, the conversion of a mixture of ethylene and a 1-olefin for example can be more difficult than the conversion of ethylene with an internal olefin, some double bond isomerization also being required in this instance.

It has also been found that branching also retards the olefin reactivity in proportion to its propinquity to the reacting double bond. Analogously, the presence of inert polar substituents on the olefinic compound appears tolerable only if located some distance from the double bond.

Thus, the present invention is directed primarily to the conversion of those olefins or combination of olefins which are capable of undergoing the olefin reaction to a significant degree when contacted with the catalyst of the present invention under reaction conditions suitable for effecting the olefin reaction.

Presently preferred olefinic feed compounds are those contained in the following classes:

1. Acyclic monoolefins, including those with aryl, cycloalkyl, and cycloalkenyl substituents, having 3-20 carbon atoms per molecule with no branching closer than about the 3- position and no quaternary carbon atoms or aromatic substitution closer than the 4- position to the double bond, and mixtures of such unsubstituted acyclic monoolefins. Some examples of these are: propylene, pentene-1, pentene-2, butene-1, butene-2, 3-methylbutene-1, hexene-2, octene-4, nonene-2, 4-methylpentene-1, decene-3, 8-ethyldecene-2, dodecene-4, vinylcyclohexane, 4-vinylcyclohexene, eicosene-1, and the like.

2. A mixture of ethylene and one or more acyclic unsubstituted internal monoolefins of (1). Some examples of such mixtures are: ethylene and butene-2, ethylene and pentene-2, ethylene and hexene-3, ethylene and heptene-3, ethylene and 4-methylpentene-2, ethylene and octene-4, ethylene and dodecene-4, and the like.

3. Acyclic, non-conjugated polyenes having from 5 to about 20 carbon atoms per molecule, containing from 2 to about 4 double bonds per molecule and having at least one double bond with no branching nearer than the 3- position and no quaternary carbon atom nearer than the 4- position to that double bond, or mixtures of such polyenes. Some examples are: 1,4-pentadiene, 1,5-hexadiene, 1,7-octadiene, 2,6-decadiene, 1,5,9-dodecatriene, 4-methylheptadiene-1,6, 1,7-octadiene, 1,6-octadiene, and the like.

4. A mixture of ethylene and one or more acyclic polyenes of (3) which contain at least one internal double bond. Some examples are: ethylene and 1,6-octadiene, ethylene and 1,5-decadiene, and the like.

5. Cyclopentene.

6. Monocyclic and bicyclic monoolefins having 7 to 12 ring carbon atoms, including those substituted with up to 3 alkyl groups having up to about 5 carbon atoms, with no branching closer than the 3- position and with no quaternary carbon atoms closer than the 4- position to that double bond, and mixtures of such olefins including mixtures with cyclopentene. Some examples are: cycloheptene, cyclooctene, 4-methylcyclooctene, 3-methyl-5-ethylcyclodecene, cyclononene, cyclodecene, norbornene, and the like.

7. A mixture of one or more of the monocyclic olefins of (6) with either ethylene or with one or more unsubstituted acyclic monoolefins of (1). Some examples of these are: ethylene and cycloheptene, ethylene and cyclooctene, propylene and cyclodecene, pentene-2 and cyclooctene, ethylene and cyclododecene, and the like.

8. Monocyclic and bicyclic non-conjugated polyenes having from 5 to about 12 ring carbon atoms, including those substituted with up to 3 alkyl groups having up to about 5 carbon atoms each, having at least one double bond with no branching closer than the 3- position and with no quaternary carbon atoms closer than the 4- position to that double bond, and mixtures thereof. Some examples of these are: 1,5-cyclooctadiene, 1,5,9-cyclododecatriene, 1,4-cycloheptadiene, norbornadiene, and the like.

9. A mixture of one or more monocyclic polyenes of (8) with one or more acyclic 1- olefins having from 2 to about 10 carbon atoms, having no branching nearer than the 3- position and no quaternary carbon atoms nearer than the 4- position to the double bond. Some examples of these are: 1,5-cyclooctadiene and ethylene, 1,5,9-cyclododecatriene and ethylene, 1,5,9-cyclododecatriene and pentene-1, and the like.

10 Polar group-substituted olefinic compounds of classes (1) through (9) containing from about 5 to about 20 carbon atoms per molecule in which the polar group, such as a halogen atom, is sufficiently removed from the active double bond (generally, no nearer to the double bond than the 5- position) so as not to interfere with the reaction, and mixtures with unsubstituted members of class (1). Some examples are: 5-chloropentene-1, a mixture of pentene-2 and 5-chloropentene-1, and the like.

According to the process of the invention, the conversion of the olefin or mixture of olefins can take place at any convenient temperature in the broad range of −30° to about 150° C., preferably 0°–75° C. The conversion can be carried out at any convenient pressure which is sufficient to maintain a liquid phase within the reaction zone. A diluent is generally preferred and a diluent such as that used in the catalyst preparation or other inert solvent can be used in the reaction if desired. In general, any inert diluent which will maintain a substantially homogeneous reaction phase can be used. The time of contact will depend upon the desired degree of conversion with the specific feed olefins and specific catalyst used but will, generally, be in the range of from about 0.1 minutes to about 20 hours, preferably 5–120 minutes. The proportion of catalyst composition to olefin feed in the reaction zone will generally be in the range of about 0.001–100 millimoles of molybdenum or tungsten per mole of olefin feed.

Any conventional contacting technique can be utilized for the olefin conversion, and batchwise or continuous operation can be utilized. After the reaction period, the products can be separated and/or isolated by conventional means such as by fractionation, crystallization, adsorption, and the like. Unconverted feed materials or products not in the desired molecular weight range can be recycled. If desired, the catalyst can be destroyed by treatment with water or alcohol, in an amount sufficient to deactivate the catalyst, prior to the separation of the products. In some cases, the catalyst can be separated from the products by distillation, crystallization, or other suitable method and recycled to the reaction zone for additional use.

The invention can be further illustrated by the following examples.

EXAMPLE I

Disproportionation of Pentene-1 Over (Triphenylphosphine)$_2$Mo(NO)$_2$Cl$_2$/Methylaluminum Sesquichloride A 1.5 millimole quantity of (triphenylphosphine)$_2$Mo(NO)$_2$Cl$_2$ was mixed with 5 ml of chlorobenzene, cooled in an ice bath, and treated with 0.2 ml of methylaluminum sesquichloride. A 6.4 g quantity of 1-pentene was then added and the mixture was allowed to react for 50 minutes, the gaseous ethylene product being allowed to vent from the system at atmospheric pressure.

The reaction mixture was then hydrolyzed and the organic phase analyzed by gas-liquid chromatography, showing the presence of 3.1 g (48%) of unreacted 1-pentene and 2.5 g (48%) of 4-octene. No other products were detected.

EXAMPLE II

Disproportionation of 1-Pentene Over NO-treated Mo(benzoate)$_2$Cl$_3$/Alkylaluminum Halides A 0.09 g quantity of Mo(benzoate)$_2$Cl$_3$ was dissolved in 10 ml of chlorobenzene and contacted with 25 psig of NO gas for 30 minutes at room temperature. The vessel was vented, releasing any ethylene formed, and then treated with 0.1 ml of methylaluminum sesquichloride followed by the addition of 10 ml of 1-pentene. The reaction mixture was allowed to react for 17 minutes and then hydrolyzed by contact with water. The gas-liquid chromatographic analyses of the organic phase showed 40.7 weight percent 1-pentene and 59.3 weight percent 4-octene.

In another similar test, a 0.09 g quantity of the molybdenum trichloride dibenzoate complex was dissolved in 10 ml chlorobenzene, contacted with gaseous NO at 25 psig for 30 minutes, treated with 0.1 ml of ethylaluminum dichloride, and reacted with 10 ml of 1-pentene for 10 minutes, the ethylene product being allowed to escape at atmospheric pressure.

After hydrolysis the organic phase was found to contain 41.9 weight percent pentenes, 1.8 weight percent hexenes, 3.4 weight percent heptenes, and 52.8 weight percent octenes.

EXAMPLE III

Disproportionation of 1-Octene Over (Pyridine)$_2$Mo(NO)$_2$Cl$_2$/Alkylaluminum Halides A 7-ounce pressure bottle was charged with 0.04 g (0.1 millimole) of (pyridine)$_2$Mo(NO)$_2$Cl$_2$ and 10 ml of chlorobenzene. The bottle was placed in a water bath maintained at 50 plus or minus 3 degrees C. and treated with 0.1 ml methylaluminum sesquichloride and 10 ml of 1-octene. The mixture was allowed to react for 25 minutes, the product ethylene being allowed to vent at atmospheric pressure.

After hydrolysis the reaction mixture was found to contain 39.7 weight percent octenes and 60.3 weight percent tetradecenes with traces of heptenes and tridecenes.

In an essentially identical run in which ethylaluminum dichloride was substituted for the methylaluminum sesquichloride, analysis of the reaction mixture showed 0.1 weight percent heptenes, 25.0 weight percent octenes, 2.5 weight percent nonenes, traces of decenes, traces of undecenes, 0.6 weight percent dodecenes, 5.2 weight percent of tridecenes, and 65.0 weight percent of tetradecenes.

In another essentially identical test in which ethylaluminum sesquichloride was substituted for the methylaluminum sesquichloride, analysis of the reaction mixture showed 0.6 weight percent heptenes, 49.8 weight percent octenes, and 49.6 weight percent tetradecenes.

EXAMPLE IV

Disproportionation of Pentene-1 Over (NO)$_2$W(triphenylphosphine)$_2$Cl$_2$/Alkylaluminum Halides A 0.17 g quantity of (NO)$_2$W(triphenylphosphine)$_2$Cl$_2$ was added to a dry pressure bottle which was capped and flushed with dry nitrogen. A 10 ml quantity of chlorobenzene was added and the mixture was cooled in an ice-water bath. A 0.2 ml quantity of methylaluminum sesquichloride was added giving a light tan-colored homogeneous solution. Ten ml of pentene-1 was added and the mixture was warmed to 50° C. After about a 2-hour reaction period, the reaction mixture was analyzed showing the presence of 0.9 weight percent ethylene, 12. weight percent propylene, 7.3 weight percent butenes, 67.5 weight percent pentenes, 8.7 weight percent hexenes, 5.3 weight percent heptenes, and 7.3 weight percent octenes.

Other similar runs, using ethylaluminum dichloride instead of methylaluminum sesquichloride, gave equal or better conversions of pentene-1 to olefinic products.

EXAMPLE V

Conversion of Propylene over (Pyridine)$_2$(NO)$_2$MoCl$_2$/EADC

A catalyst was prepared by mixing 0.19 g (pyridine)$_2$(NO)$_2$MoCl$_2$, 100 ml of chlorobenzene, and 0.38 g ethylaluminum dichloride (EADC). This mixture was charged to an autoclave along with 59 g of propylene. The autoclave had previously been flushed with 100 ml of chlorobenzene containing 1 ml ethylaluminum dichloride.

The above-described reaction mixture was stirred in the autoclave for about 1 hour at a temperature of about 50° C. and at autogenous pressures of 165–265 psig. At the end of this reaction period samples were taken from both the gas phase and the liquid phase within the reactor. The gases were then vented and the liquid phase of the reaction mixture was treated with an isopropanol solution of 2,2'-methylene-bis(4-methyl-6-tert-butylphenol). The isopropanol addition precipitated a polymeric product. After drying under vacuum, the polymer weighed 2.8 g and was rubber-like in character. An infrared examination of the polymer indicated that it contained an estimated 15 to 20 percent of propylene present in a head to tail configuration.

The samples taken from the reactor were analyzed by gas-liquid chromatography and showed the following:

|  | Ethylene | Propylene | Butenes |
| --- | --- | --- | --- |
| gas sample | 22.5 wt % | 70.5 wt % | 7.0 wt % |
| liquid sample | 9.4 wt % | 68.7 wt % | 21.8 wt % |

The preceding show that the catalyst system described is capable not only of disproportionating propylene to ethylene and butenes, but of producing, at least in small amounts, a rubbery copolymer of ethylene and propylene.

EXAMPLE VI

Cyclooctene was contacted with di(triphenylphosphine) molybdenum dinitrosyl dichloride and methylaluminum sesquichloride as the catalyst. The di(triphenylphosphine) molybdenum dinitrosyl dichloride was prepared as described in *Inorganic Chemistry* 3, No. 11, 1609–1612 (1964). Briefly, Mo(CO)$_6$ was dissolved in chlorobenzene, nitrosyl chloride was bubbled through to precipitate Mo(NO)$_2$Cl$_2$, which was dissolved in benzene and heated with two equivalents of triphenylphosphine. The reaction product was removed by evaporating the benzene. The amounts of materials were as follows:

| | |
| --- | --- |
| Cyclohexane, parts by weight | 234 |
| Cyclooctene, parts by weight | 100 |
| ($\phi_3$P)$_2$Mo(NO)$_2$Cl$_2$, mhm | 1.07 |
| Methylaluminum sesquichloride, mhm | 12.0 | mhm = gram millimoles per 100 grams olefin

When conducting the reaction, cyclohexane was charged to the reactor first and then the di(triphenylphosphine) molybdenum dinitrosyl dichloride. The reactor was then purged with nitrogen, closed, and flushed with argon. Cyclooctene was then added and finally the methylaluminum sesquichloride. The reaction mixture was agitated at room temperature for 15 minutes. The temperature was increased to 50° C. and maintained at this level for 48 hours. The reaction was terminated with a 10 weight percent solution of 2,2'-methylene-bis(4-methyl-6-tert-butylphenol) in isopropyl alcohol, the amount used being sufficient to provide one part by weight of the antioxidant per 100 parts by weight of cyclooctene charged to the reactor. The mixture was poured into isopropyl alcohol, with stirring, to coagulate the product. The product was pressed dry with paper towels, redissolved in cyclohexane, and coagulated again with isopropyl alcohol. It was dried at 60° C. in a stream of nitrogen. A conversion of 32 percent was obtained. The product was a soft rubber. It was gel free and had an inherent viscosity of 1.22, unsaturation by IC1 titration of 96 percent, and a melting point (determined by differential thermal analysis) of 38° C. It was analyzed by gel permeation chromatography and found to have a heterogeneity index of 8.8. This value showed that the polymer had a wide molecular weight distribution. Infrared examination showed a 2:1 trans:cis configuration with no indication of vinyl unsaturation.

EXAMPLE VII

Cyclopentene was contacted with di(triphenylphosphine) molybdenum dinitrosyl dichloride and methylaluminum sesquichloride as the catalyst. The amounts of materials were as follows:

| | |
|---|---|
| Cyclohexane, parts by weight | 390 |
| Cyclopentene, parts by weight | 100 |
| ($\phi_3$P)$_2$Mo$_2$(NO)$_2$Cl$_2$, mhm | 1.3 |
| Methylaluminum sesquichloride, mhm | 15 |

The order of charging the several ingredients was the same as in Example IX. After charging was completed, the temperature of the mixture was held at 75° F. for 24 hours. The mixture was agitated occasionally during this period. The reaction was terminated as in Example I and the product was recovered by coagulation in isopropyl alcohol. It was dried at 60° C. in a stream of nitrogen. A conversion of 19 percent was obtained. The product was a tough rubber. It was gel free and had an inherent viscosity of 4.17, unsaturation of 96 percent (IC1 titration) and a heterogeneity index of 12.7 which indicated a wide molecular weight distribution. An infrared film scan showed a large amount of trans configuration.

EXAMPLE VIII

A preformed catalyst was employed for the conversion of cyclopentene. The amounts of materials were as follows:

| | |
|---|---|
| Toluene, parts by weight | 435 |
| Cyclopentene, parts by weight | 100 |
| ($\phi_3$P)$_2$Mo(NO)$_2$Cl$_2$, mhm | 1.3 |
| Methylaluminum sesquichloride, mhm | 1.77 |

The reactor was charged with toluene and then purged with nitrogen. The di(triphenylphosphine) molybdenum dinitrosyl dichloride was added and the reactor was closed, flushed, and pressured to 20 psig with nitrogen. The reactor contents were cooled to 0° C. in an ice bath, methylaluminum sesquichloride was added, and the temperature was adjusted to 5° C. and held at this level for 1.5 hours. Cyclopentene was then charged and the temperature was maintained at 5° C. for 20.5 hours. The reaction was terminated with 2,2'-methylene-bis(4-methyl-6-tert-butylphenol) as in Example IX and the product was coagulated with isopropyl alcohol. It was separated and dried at 60° C. in a stream of nitrogen. A conversion of 61 percent was obtained. The product was a gel free, tough rubber with an inherent viscosity of 8.25 and unsaturation of 96.8 percent. An infrared film scan showed that the polymer was predominantly trans.

EXAMPLE IX

Substantially pure 1,5-hexadiene was contacted with bis(triphenylphosphine) dinitrosyldichloromolybdenum with methylaluminum sesquichloride as adjuvant in chlorobenzene diluent at atmospheric pressure and room temperature for 16 hours. The following products were identified:

| | |
|---|---|
| Ethylene | 11.3 weight per cent |
| 1,5,9-decatriene | 25.6 weight per cent |
| C$_{14}$ tetraene | 10.2 weight per cent |
| C$_{18}$ pentaene | 8.7 weight per cent |
| 1,5-hexadiene | 44.0 weight per cent |

The above shows that 1,5-hexadiene was effectively disproportionated in the homogeneous catalyst system.

EXAMPLE X

Using the same catalyst system as in Example IX, 1,7-octadiene was converted to cyclohexene and ethylene in 95 percent yield at room temperature and pressure. This shows that an acyclic polyene is converted into a cyclic polyene and ethylene.

EXAMPLE XI

A mixture of cyclooctene and ethylene was contacted with catalyst and adjuvant as in Examples IX and X at room temperature and 25 psi pressure to yield 13 weight percent 1,9-decadiene. This shows that ethylene and a cyclic olefin are converted to an acyclic polyene.

EXAMPLE XII

Using the same catalyst and adjuvant system as in the previous three examples, 1,4-pentadiene was converted to 1,4-cyclohexadiene and ethylene at room temperature and atmospheric pressure. This example shows that acyclic dienes can be converted to cyclic dienes according to the process of the invention.

EXAMPLE XIII

Conversion of Propylene over (Pyridine)$_2$Mo(NO)$_2$Cl$_2$/EADC

A catalyst was prepared from 0.19 g (0.5 millimole) of (C$_5$H$_5$N) Mo(NO)$_2$Cl$_2$, 100 ml of chlorobenzene and 0.38 g (0.003 millimole) of ethylaluminum dichloride (EADC). This was charged to the 300 cc autoclave along with 65 g of propylene. The mixture was reacted for 2 hours at 45°–50° C. and at 210–260 psig.

A sample was taken from the reactor after 35 minutes of the reaction period. A gas-liquid chromatographic (GLC) examination of the volatile materials in this sample showed the presence of 11.7 percent ethylene, 76.4 percent propylene, and 11.9 percent butenes, by weight.

After the full reaction period, the reactor was vented through dryice cooled traps and the resulting mixture was found to contain, besides ethylene, propylene and butenes, a polymer which was a mixture of ethylene and propylene.

EXAMPLE XIV

Conversion of Pentene-2 over (triphenylphosphine)$_2$Mo(NO)$_2$Cl$_2$/AlCl$_3$—LiAlH$_4$ A 0.1 g quantity of (triphenylphosphine)$_2$Mo(NO)$_2$Cl$_2$ was charged to a 7-ounce reaction vesel together with 15 cc chlorobenzene and 0.1 g anhydrous AlCl$_3$ under an inert atmosphere. The mixture was allowed to stand overnight at room temperature and then treated with 0.1 g LiAlH$_4$ followed by stirring 1 hour at room temperature and 0.5 hour at 70° C. The mixture was cooled to room temperature and 3 cc pentene-2 was added and allowed to stir for 2 hours. Analysis (GLC) of the reaction mixture, after hydrolysis with water, showed that it contained about 5 percent butenes, 87 percent pentenes, and 8 percent hexenes by weight.

EXAMPLE XV

Conversion of 1-Octene over NO-treated (Butyronitrile)$_2$MoCl$_4$/MASC in Benzene A 1.9 g quantity of (butyronitrile)$_2$MoCl$_4$ and 25 ml benzene was treated with 30 psig nitric oxide for 2 hours at room temperature producing a solution having a green-black color. A 5 ml quantity of this solution was then charged into a 7-ounce reaction vessel and contacted with 0.5 ml methylaluminum sesquichloride (MASC) and 5 ml octene-1. The reaction was allowed to continue, with stirring, for 45 minutes at room temperature and the evolved ethylene was allowed to vent. The mixture was hydrolyzed and the organic phase was found to contain, by GLC, 41.4 percent C$_8$ olefin, 0.4 percent C$_9$ olefin, 1.6 percent C$_{13}$ olefin, and 56.6 percent C$_{14}$ olefin, by weight.

EXAMPLE XVI

Conversion of 1-Octene over NO-treated (Cyclopentadienyl)Mo(CO)$_3$I/MASC

In a manner similar to that of preceding examples, a mixture of 0.19 g of (cyclopentadienyl)Mo(CO)$_3$I in 10 ml chlorobenzene was treated with NO for 1 hour at 25 psig, followed by venting and evacuation of the vessel. A 0.2 ml quantity of methylaluminum sesquichloride (MASC) was then added, followed by 10 ml of 1-octene. The mixture was stirred for 4 hours and 10 minutes at room temperature, hydrolyzed, and analyzed (GLC) showing 82.4 percent C$_8$ olefin and 17.4 percent C$_{14}$ olefin, by weight. The ethylene was vented.

EXAMPLE XVII

Conversion of 1-Pentene over NO-treated (Stearate)$_2$MoCl$_3$/EADC

In a similar manner, a mixture of 0.4 millimole of (stearate)$_2$MoCl$_3$ in 50 ml chlorobenzene was treated with NO at 25 psig for 30 minutes, followed by venting and evacuation of the treatment vessel. A 25 ml quantity of the solution was stirred with 0.2 ml ethylaluminum dichloride (EADC) and 20 ml 1-pentene for 4 minutes at room temperature. After hydrolysis, the mixture was found (by GLC) to contain 1.4 percent C$_2$ olefin (most had been allowed to vent), 1.0 percent C$_3$ olefin, 2.5 percent C$_4$ olefin, 57.8 percent C$_5$ olefin, 1.5 percent C$_6$ olefin, 1.8 percent C$_7$ olefin, and 33.8 percent C$_{14}$ olefin.

EXAMPLE XVIII

Conversion of 1-Pentene over NO-treated MoO$_2$(acetylacetonate)$_2$/MASC

A mixture of 0.2 g of MoO$_2$(acetylacetonate)$_2$ and 10 ml chlorobenzene was treated with NO for 30 minutes at 25 psig and at room temperature. The treatment vessel was then vented and evacuated. A 0.2 ml quantity of methylaluminum sesquichloride was then added followed by 10 ml of 1-pentene. After 1 hour, the mixture was hydrolyzed and analyzed (GLC) to show 82.1 percent 1-pentene and 17.9 percent 4-octene, by weight. The ethylene product had been allowed to vent.

EXAMPLE XIX

Conversion of Pentene-1 over NO-treated MoOCl$_3$/MASC

A 7-ounce reaction vessel was charged with 0.11 g MoOCl$_3$ and 10 ml chlorobenzene followed by treatment with NO at 25 psig for 30 minutes at room temperature. After venting and evacuation, 0.2 ml of methylaluminum sesquichloride and 5 ml pentene-1 were added and allowed to react for 30 minutes. After hydrolysis, the reaction mixture was found (by GLC) to contain 37.3 percent C$_5$ olefin, 2.9 percent C$_6$ olefin, 4.9 percent C$_7$ olefin, and 54.8 percent C$_8$ olefin, by weight. The ethylene product had been allowed to vent.

EXAMPLE XX

Conversion of Pentene-1 over NO-treated Tetraallyltin-treated MoCl$_5$/MASC

A mixture of 0.27 g MoCl$_5$, 20 ml chlorobenzene, and 0.28 g tetraallyltin was treated with NO at 25 psig for 30 minutes and at room temperature. After venting and evacuation, one half of the above-prepared solution was charged to a 7-ounce reaction vessel and mixed with 0.5 ml methylaluminum sesquichloride (MASC) and 10 ml 1-pentene. After 10 minutes, the mixture was hydrolyzed and analyzed by GLC showing 18.1 percent C$_5$ olefins, 1.8 percent C$_6$ olefins, 2.0 percent C$_7$ olefins, and 77.9 percent C$_8$ olefins, by weight. The ethylene product had been allowed to vent.

EXAMPLE XXI

Conversion of Pentene-1 over NO-treated (Stearate)$_2$MoCl$_3$/MASC in Cyclohexane A mixture of 0.8 millimoles of (stearate)$_2$MoCl 3 in 40 ml cyclohexane was treated with NO at 25 psig for 1 hour. After venting and evacuation, 5 ml of the above-treated solution was charged into a 7-ounce reaction vessel together with 5 ml cyclohexane, 0.1 ml methylaluminum sesquichloride (MASC), and 10 ml pentene-1. After 2 hours the mixture was hydrolyzed and analyzed by GLC showing 66.1 percent pentene-1, and 33.9 percent 4-octene, by weight, neglecting the ethylene which was allowed to vent.

In a similar fashion, three more room temperature tests were made in which the catalytic adjuvant was varied. Ethylaluminum sesquichloride (EASC) and diethylaluminum chloride (DEAC) were used. The essential data and results are shown in the table below:

|  | Test A | Test B | Test C |
|---|---|---|---|
| Cyclohexane, ml | 5 | 5 | 5 |
| Adjuvant, ml | MASC, 0.1 | EASC, 0.2 | DEAC, 0.2 |
| Above prepared solution, ml | 5 | 5 | 5 |
| Feed olefin, ml | 1-octene, 10 | 1-pentene, 10 | 1-pentene, 10 |
| Reaction period, hour | 2 | 1 | 1 |
| Analysis of reaction mixture olefin, wt % | 1-octene, 86.4%<br>7-tetradecene, 13.6% | 1-pentene, 72%<br>4-octene, 28% | 1-pentene, 96.5%<br>4-octene, 3.5% |

EXAMPLE XXII

Conversion of Pentene-1 or Octene-1 over NO-treated Pyridine-treated $WCl_6$/MASC or EADC A tungsten complex-containing solution was prepared by treating 0.4 g $WCl_6$ in 20 ml chlorobenzene with NO at 25 psig for 1 hour. The treatment vessel was then vented, evacuated, and treated with 0.24 g pyridine.

The above prepared tungsten solution was then used to convert olefins in several 1 hour runs carried out at room temperature. The essential data and results of these runs are shown in the table below.

|  | Run A | Run B |
|---|---|---|
| Tungsten solution, ml | 2 | 2 |
| Chlorobenzene, ml | 8 | 8 |
| MASC, ml | 0.2 |  |
| EADC, ml |  | 0.2 |
| Pentene-1, ml | 10 | 10 |
| Reaction mixture analysis* Olefin, wt. % | $C_5$, 79.8%<br>$C_6$, —<br>$C_7$, 0.4%<br>$C_8$, 19.7% | $C_5$, 57.8%<br>$C_6$, 3.0%<br>$C_7$, 4.3%<br>$C_8$, 34.9% |

*excluding ethylene which was allowed to vent

When the above runs were repated with octene-1 feed olefin, the reaction mixture analysis was as follows:

| 1-octene, 83.4% | $C_7$, 2.3% |
|---|---|
| 7-tetradecene, 16.6% | $C_8$, 67.2% |
|  | $C_9$, 1.1% |
|  | $C_{10}$, 1.0% |
|  | $C_{12}$, 0.1% |
|  | $C_{13}$, 1.2% |
|  | $C_{14}$, 27.2% |

EXAMPLE XXIII

Conversion of Octene-1 over NOCl-treated Pyridine-treated $MoO_2$/MASC

A mixture of 0.13 g of $MoO_2$ in 10 ml chlorobenzene was treated with NOCl at 10 psig for 2 hours at room temperature. The treatment vessel was then vented and evacuated, and 5 ml of the above prepared mixture was charged to a 7-ounce reaction vessel followed by 5ml chlorobenzene, 0.8 g pyridine, 0.5 ml methylaluminum sesquichloride and 10 ml 1-octene.

After a 2 hour reaction period at room temperature during which the ethylene product was allowed to vent, the reaction mixture was hydrolyzed and analyzed by GLC. The reaction mixture was found to contain 1.1 percent $C_7$ olefin, 65.1 percent $C_8$ olefin, 0.4 percent $C_9$ olefin, 0.6 percent $C_{13}$ olefin, and 32.8 percent $C_{14}$ olefin.

EXAMPLE XXIV

Conversion of Ethylene and 1,5-cyclooctadiene over (Triphenylphosphine)$_2$Mo(NO)$_2$Cl$_2$/MASC Into a 500 ml autoclave was charged 0.1 g (triphenylphosphine)$_2$Mo-(NO)$_2$Cl$_2$ and 50 ml chlorobenzene. The reactor was flushed with ethylene and 0.2 ml methylaluminum sesquichloride and 6 ml 1,5-cyclooctadiene were then added. The reactor was pressured with 500 psig ethylene and the reactants were stirred for 4 hours at room temperature. The reactor contents were then hydrolyzed and analyzed by GLC showing the reaction mixture to contain 0.6 percent 1,5-hexadiene, 70.0 percent 1,5-cyclooctadiene, and 29.4 percent 1,5,9-decatriene by weight.

EXAMPLE XXV

Additional Olefin Conversions over (triphenylphosphine)$_2$Mo(NO)$_2$Cl$_2$/MASC In a manner similar to the preceding examples, the catalyst system (triphenylphosphine)$_2$Mo(NO)$_2$Cl$_2$/MASC was used to convert:

a. 1,7-octadiene to other olefinic products including cyclohexene and 1,7,13-tetradecatriene, b. Cyclooctene and pentene-2 to other olefinic products including dodecadiene, tridecadiene, and tetradecadiene, c. Cyclododecene and ethylene to other olefinic products including 1,13-tetradecadiene, d. 1,5,9-cyclododecatriene and ethylene to other olefinic products including 1,5,9,13-tetradecatetraene, 1,5-hexadiene, and 1,5,9-decatriene, e. 4-vinylcyclohexene and pentene-2 to other olefinic products including 1,2-bis3-cyclohexene-1-yl)ethylene, propenylcyclohexene, and butenylcyclohexene, f. 4-vinylcyclohexane and pentene-2 to other olefinic products including 1,2-bis(cyclohexyl)ethylene, propenylcyclohexane, and butenylcyclohexane, g. Octene-4 and ethylene to other olefinic products including butenes, pentenes, and hexenes, and h. Ethylene and a mixture of nonenes, decenes, undecenes, dodecenes, and tridecenes to other olefinic products including hexenes, heptenes, and octenes.

EXAMPLE XXVI

Disproportionation of 1-Octene over NOCl- and Pyridine-treated $MoS_2$/MASC

In a manner similar to the preceding examples, 0.32 g of $MoS_2$ in 20 ml chlorobenzene was pressured with NOCl at 10 psig and then heated at 50°–55° C. for 1.5 hours. The solution was then cooled and evacuated. A 5 ml quantity was then transferred to a reaction flask together with 5 ml chlorobenzene, 0.8 g pyridine, 0.5 ml MASC, and 10 ml 1-octene.

This mixture was stirred for 2 hours at room temperature and then hydrolyzed. Analysis of the mixture showed the following:

| Olefin | Wt. % |
| --- | --- |
| $C_7$ | 0.1 |
| $C_8$ | 96.5 |
| $C_9$ | 0.1 |
| $C_{13}$ | 0.1 |
| $C_{14}$ | 2.5 |
| Unknown | 0.6 |

EXAMPLE XXVII

Conversion of Pentene-1 Over $Mo(NO)_2Cl_2$/MASC

A 0.25 millimole quantity of $Mo(NO)_2Cl_2$ ml chlorobenzene was diluted with an additional 10 ml chlorobenzene and treated with 0.1 millimole methylaluminum sesquichloride in a glass reaction bottle. This mixture was cooled in an ice bath for about 13 minutes and then 10 ml pentene-1 was added. This reaction mixture was maintained in the bath for 1 hour and 10 minutes during which time the ethylene, which was formed as a product of the reaction, was allowed to vent. The reaction mixture was then hydrolyzed and analysis of the organic phase showed the presence of 21 weight percent recovered pentene-1, 25 weight percent octene-4, with the remainder being heavier materials. These data show that a nitrosyl group-containing complex of molybdenum is useful for olefin disproportionation even in the absence of other ligands in the complex.

EXAMPLE XXVIII

Conversion of Pentene-2 Over $(NO)_2Mo(triphenylphosphine)_2Cl_2/AlCl_13$

In a pressure bottle were placed 0.1 gram of anhydrous aluminum chloride, 0.1 gram of $(NO)_2Mo(triphenylphosphine)_2Cl_2$ and 20 ml of chlorobenzene. The material was stirred for 1 hour at room temperature and a dark green solution, with some undissolved aluminum, was obtained. The material was then heated to 65° C. and maintained at this temperature for 5 hours. A homogeneous yellow-brown solution resulted.

After standing overnight the solution was treated with 5.0 ml of pentene-2 and stirred at room temperature. After 2 hours, conversion to butenes and hexenes was found to be 1%, by GLC analysis. After 7 hours conversion was 14% and after 26 hours conversion was 29%.

The above data show that aluminum chloride is an effective adjuvant.

The metals referred to herein are in accordance with the Periodic Table of Elements appearing in Handbook of Chemistry and Physics, Chemical Rubber Company, 45th Edition (1964), page B-2.

In the practice of the process of this invention, the feed olefins, catalysts and operating conditions disclosed include combinations wherein solid, rubbery materials are produced; for example, if a propylene feed and a suitable aluminum-containing adjuvant such as an organoaluminum dihalide or an organoaluminum sesquihalide are used, a solid, rubbery material is produced having characteristics of ethylene-propylene rubber. This rubbery material is useful in the manufacture of tires, wire coating, footwear and other industrial products.

The homogeneous catalysts of this invention can be deposited upon a suitable support or carrier and used in the olefin reaction, preferably where the olefin feed is in the vapor phase. Catalyst supports include solid, inorganic or organic materials conventionally used as catalyst supports or carriers such as silica, alumina, silica-alumina, titania, boria, zeolites, ion exchange resins, solid polymers containing functional groups such as those prepared by the polymerization of 4-vinylpyridine, vinyl dimethylphosphine, and the like.

The support can be impregnated with the homogeneous catalyst by wetting the support with a solution of the catalyst in a solvent which is then evaporated. The support can also be impregnated with either the (a) or (b) component and the remaining component can be added later. For example, the solid support material can be impregnated with the (a) component and the resulting composite conveniently stored until required. Just prior to use, the composite can be treated with the (b) component, or, if the reaction is in the liquid phase, the (b) component can simply be added to the reaction zone. Among impregnation solvents suitable are relatively low-boiling organic solvents such as pentane, methylene chloride, cyclohexane, and the like. The amount of homogeneous catalyst added to the support will be from 0.1 to about 30 weight percent of the total of the catalyst and support. If the support is to be activated by calcination, it is usually activated prior to the impregnation step.

Impregnation and evaporation conditions in preparing the catalyst are conventional, being carried out at temperatures up to about 150° C. Operating conditions in carrying out the olefin reaction are the same for the supported and the nonsupported homogeneous catalyst systems.

I claim:
1. A process for converting a feed olefin hydrocarbon having non-tertiary unsaturation selected from the group consisting of:
   1. acyclic monoolefins, including those with aryl, cycloalkyl, and cycloalkenyl substituents, having 3–20 carbon atoms per molecule with no branching closer than about the 3- position and no quaternary carbon atoms or aromatic substitution closer than the 4- position to the double bond, and mixtures of such unsubstituted acyclic monoolefins;
   2. a mixture of ethylene and one or more acyclic unsubstituted internal monoolefins of (1);
   3. acyclic, nonconjugated polyenes having from 5 to about 20 carbon atoms per molecule, containing from 2 to about 4 double bonds per molecule and having at least one double bond with no branching nearer than the 3- position and no quaternary carbon atom nearer than the 4- position to that double bond, or mixtures of such polyenes;
   4. a mixture of ethylene and one or more acyclic polyenes of (3) which contain at least one internal double bond;
   5. a mixture of one or more monocyclic or bicyclic monoolefins having 7 to 12 ring carbon atoms, including those substituted with up to 3 alkyl groups having up to about 5 carbon atoms, with no branching closer than the 3- position and with no quaternary carbon atoms closer than the 4- position to that double bond with either ethylene or with one or more unsubstituted acyclic monoolefins of (1);
6. monocyclic and bicyclic nonconjugated polyenes having up to 12 ring carbon atoms, including those substituted with up to 3 alkyl groups having up to about 5 carbon atoms each, having at least one double bond with no branching closer than the 3-position and with no quaternary carbon atoms closer than the 4- position to that double bond, and mixtures thereof;
7. a mixture of one or more monocyclic polyenes of (6) with one or more acyclic 1- olefins having from 2 to about 10 carbon atoms, having no branching nearer than the 3- position and no quaternary carbon atoms nearer than the 4- position to the double bond;
8. polar group-substituted olefinic compounds of classes (1) through (7) containing from about 5 to about 20 carbon atoms per molecule in which the polar group, such as a halogen atom, is sufficiently removed from the active double bond (generally, no nearer to the double bond than the 5- position) so as not to interfere with the reaction, and mixtures with unsubstituted members of class (1);

which comprises contacting said feed olefin hydrocarbon with a catalyst system which forms on admixture of
a. a metal complex represented by the formula $[(L)_a M_b (NO)_c Z_d]_x$ wherein M is molybdenum or tungsten; each Z is a halogen, CN, SCN, OCN, $SnCl_3$ or a hydrocarbon carboxylic acid radical having 1 to about 30 carbon atoms; L is a ligand represented by the formula
$R_3Q$; $R_3QO$; $R_2Q-QR_2$; CO; NO; O; S;

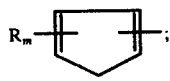

$R_3N$; $R_2N-R^2-NR_2$

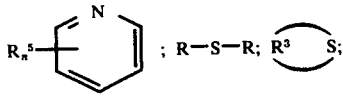

$(CHR^4=CR^4-CH_2)$;
$R(CN)_b$;

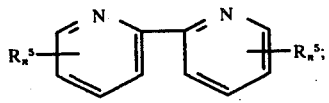

$(R_2NCSS)$;
$[(RCO)_2CH$; and $R(COO)_b$;
wherein each R is a saturated aliphatic or aromatic hydrocarbon radical including alkoxy and halo derivatives thereof, having up to 20 carbon atoms; each Q is phosphorous, arsenic, or antimony; $R^2$ is a divalent saturated aliphatic or aromatic hydrocarbon radical having up to 20 carbon atoms; $R^3$ is a saturated or ethylenically unsaturated divalent hydrocrbon radical having 3 to 10 carbon atoms; each $R^4$ is a hydrogen or a methyl radical; each $R^5$ is an aromatic, saturated aliphatic, or ethylenically unsaturated hydrocarbon radical having up to 20 crbon atoms; m is 0–5, n is 0–3, a is 0–3, b is 1–2, c is 1–2 and d is 0–5; and the number of (L), NO, and Z groups present in the complex is not greater than the number required for the metal to achieve the closed shell electronic configuration of the next higher atomic number inert gas; and x is the number of the polymeric state of the compound; and
b. an aluminum containing adjuvant which is:
1. $R_e AlX_f$,
2. a mixture of compounds of 1),
3. a mixture of one or more of $AlX_3$ or $R_e AlX_f$ compounds with one or more compounds having the formula $R_g^1 M^1 X_h$, or
4. an $AlX_3$ compound, wherein each R is as defined above; each $R^1$ is hydrogen or R; each X is a halogen; each $M^1$ is a metal of Group I-A, II-A, II-B or III-A; e is 1, 2 or 3, f is 0, 1 or 2, the sum of e and f being 3; g is 1, 2 or 3, h is 0, 1 or 2, the sum of g and h being equal to the valence of $M^1$, and wherein the molar proportion of (b) to (a) is in the range of from about 0.1:1 to about 20:1.

2. The process of claim 1 wherein the conditions for the olefin reaction include a temperature in the range of about −30° to about 150° C. and a pressure which is sufficient to maintain a liquid phase within the reaction zone.

3. The process of claim 2 wherein said temperature is in the range of 0° to 75° C.

4. The process of claim 1 wherein the reaction is accomplished in the presence of an inert diluent in which both the (a) and (b) components of the catalyst are at least partially soluble.

5. The process of claim 1 wherein the catalyst further includes a solid inorganic or organic support or carrier selected from the group consisting of silica, alumina, silica-alumina, titania, boria, zeolites, ion exchange resins and solid polymers containing functional groups.

6. The process of claim 2 wherein the (a) component is (triphenylphosphine)$_2$Mo(NO)$_2$Cl$_2$ and the (b) component is methylaluminum sesquichloride, a mixture of AlCl$_3$ and LiAlH$_4$, or AlCl$_3$.

7. The process of claim 2 wherein the (a) component is NO complexed with Mo(benzoate)$_2$Cl$_3$ and the (b) component is methylaluminum sesquichloride or ethylaluminum dichloride.

8. The process of claim 2 wherein the (a) component is (pyridine)$_2$Mo(NO)$_2$Cl$_2$ and the (b) component is methylaluminum sesquichloride, ethylaluminum dichloride or ethylaluminum sesquichloride.

9. The process of claim 2 wherein the (a) component is (NO)$_2$W(triphenylphosphine)$_2$Cl$_2$ and the (b) component is methylaluminum sesquichloride or ethylaluminum dichloride.

10. The process of claim 2 wherein the (a) component is NO complexed with (butyronitrile)$_2$MoCl$_4$, NO complexed with (cyclopentadienyl)Mo(CO)$_3$I, NO complexed with MoO$_2$(acetylacetonate)$_2$, NO complexed with MoOCl$_3$, or NO and tetraallyltin complexed with MoCl$_5$, and (b) is methylaluminum sesquichloride.

11. The process of claim 2 wherein the (a) component is NO and pyridine complexed with WCl$_6$ and the (b) component is methylaluminum sesquichloride or ethylaluminum dichloride.

12. The process of claim 2 wherein the (a) component is NO complexed with (stearate)$_2$MoCl$_3$ and the (b) component is methylaluminum sesquichloride, ethylaluminum dichloride, ethylaluminum sesquichloride or diethylaluminum chloride.

13. The process of claim 2 wherein the (a) compartment is Mo(NO)$_2$Cl$_2$ and the (b) component is methylaluminum sesquichloride.

* * * * *

UNITED STATES PATENT OFFICE
CERTIFICATE OF CORRECTION

PATENT NO. : 4,010,217

DATED : March 1, 1977

INVENTOR(S) : Ernest A. Zuech

It is certified that error appears in the above-identified patent and that said Letters Patent are hereby corrected as shown below:

Column 21, line 40, after "$R_2N-R^2-NR_2$" insert --- ; ---;
           line 57, after "$[(RCO)_2CH$" insert --- } ---;
           line 61, delete "phosphorous" and insert --- phosphorus ---.
Column 22, lines 66 & 67, delete "compartment" and insert --- component ---

Signed and Sealed this

*fifth* Day of *July 1977*

[SEAL]

Attest:

RUTH C. MASON
*Attesting Officer*

C. MARSHALL DANN
*Commissioner of Patents and Trademarks*